United States Patent [19]

Nielsen

[11] Patent Number: 4,765,979

[45] Date of Patent: Aug. 23, 1988

[54] METHOD AND COMPOSITION FOR KILLING TERRESTRIAL MOLLUSCS

[76] Inventor: James W. Nielsen, P.O. Box 6669, Brookings, Oreg. 97415

[21] Appl. No.: 838,329

[22] Filed: Mar. 11, 1986

[51] Int. Cl.$^4$ ...................... A01N 25/00; A01N 59/06
[52] U.S. Cl. ........................................ 424/84; 424/154
[58] Field of Search .................................. 424/84, 154

[56] References Cited

U.S. PATENT DOCUMENTS

| | | | |
|---|---|---|---|
| 3,048,516 | 8/1962 | Mosca | 424/154 |
| 3,090,723 | 5/1963 | Pastac | 424/84 |
| 4,058,626 | 11/1977 | Roth | 514/705 |

OTHER PUBLICATIONS

The Merck Index, 10th ed., #8511 (1983).

*Primary Examiner*—Albert T. Meyers
*Assistant Examiner*—John M. Kilcoyne

[57] ABSTRACT

A molluscicide composition is provided which is highly effective and environmentally safe. The composition includes a carrier compound, an attractant, and a molluscicide agent. The attractant consists of metaldehyde and the molluscicide agent consists of atomized powdered elemental aluminum. Wheat, barley, oats, corn and mill-run bran are used as the carrier compounds. In a preferred form of the invention, a preservative, a dispersing agent and water are added to enhance the preparation and stability of the composition. The composition may be applied in meal, pellet, cake or slurry form. It is highly effective in killing terrestrial molluscs (slugs and snails) while avoiding the environmental and efficacy problems of other molluscicide compositions, including those using metaldehyde as the sole molluscicide agent.

1 Claim, No Drawings

METHOD AND COMPOSITION FOR KILLING TERRESTRIAL MOLLUSCS

BACKGROUND OF THE INVENTION

The present invention generally relates to a molluscicides, and more particularly to a molluscicide having an effective and an environmentally safe low dose mollusc killing active ingredient.

Slugs and snails Terrestrial Gastropod Molluscs are capable of causing extensive damage to Horticultural Ornamental plants and Agriculture food crops. They are omnivorous, consuming leaves, bulbs, tubers, fungi, lichens, algae and animal matter. Agricultural food crops extensively damaged by terrestrial molluscs include leafy vegetables, green beans and strawberries. Fruit and fruit trees and the like are extensively damaged, as is horticultural gardening and ornamental plants. Animal crops such as hay and clover are also extensively damaged by molluscs. Tests have shown that a slug or snail can consume its own weight in food materials in a matter of days.

Slugs and snails are closely related members of the phylum mollusca. Snails have a large external shell used for protection against predators and adverse climatic conditions. However, snails require a living environment containing large quantities of calcium containing materials, including lime ($CaCO_3$). Calcium containing materials are necessary for the snail to develop its shell. Therefore, most snails are found in areas having soil rich in calcium.

Slugs do not have an external shell and do not require calcium rich soil to survive. Although slugs are capable of burrowing into the earth for food and shelter, they are vulnerable to desiccation and death in open and unshaded areas. Therefore slugs primarily subsist in high moisture climates. In the United States, the Pacific Northwest provides moist condition conducive to slug survival and propagation.

Slugs and snails, if uncontrolled can propagate at a rapid rate, causing enormous horticultural and agricultural damage. Because they are semi-nocturnal, they often avoid capture by predators. Most slug and snail predators, including birds, actively feed during day light hours only. The agricultural problems caused by slugs and snails were recognized and reported in the early years of the twentieth century. For example, the state of Oregon recognized the potential damage from slug infestation in 1911. In that year, Oregon initiated studies involving slug control. Work done through the year 1919 resulted in a method of controlling slug using a composition having an attractant (lettuce) combined with calcium arsenate, an environmentally hazardous poison.

Nearly 15 years later, another chemical molluscicide was discovered which is still in use today. This substance is metaldehyde which is a polymer of acetaldehyde with the empirical formula $C_8H_{16}O_4$. Metaldehyde is formed by the polymerization of four to six acetaldehyde molecules. Metaldehyde has a characteristic vinegar-like odor which is highly attractive to slugs and snails. By either ingestion or external contact, metaldehyde causes a brief period of paralysis followed by stimulation of the mucus-secreting glands in the slugs or snails. Such stimulation of the mucus secreting glands results in the production of large quantities of viscid slime. Excessive slime production, in combination with desiccation by the sun during daylight hours, causes death by dehydration.

However, metaldehyde has numerous safety and efficacy problems. First, metaldehyde is toxic to both humans and animals. In most commercial formulations, 2-4% by weight metaldehyde is used. This amount is potentially harmful when used around humans and animals.

Furthermore, the efficacy of metaldehyde as a molluscicide is limited. It is only effective under certain environmental conditions. For metaldehyde to function, dry, warm and sunny conditions must be present. These conditions enhance the desiccating effects caused by metaldehyde. However, when moist, overcast conditions exist, snails and slugs can overcome the desiccating effects of metaldehyde, by excreting the material from their bodies in a matter of days. Without enhanced desiccation by the sun, the effectiveness of metaldehyde is limited. In fact, tests indicate that slugs and snails, after intoxication with metaldehyde, will actively seek shaded areas and soil high in moisture to overcome the effects of metaldehyde.

Metaldehyde also has limited effectiveness in killing juvenile slugs and snails. The scientific mechanism behind this problem is presently unknown. Finally, metaldehyde is relatively expensive, selling for approximately $3.50 per pound. Such cost can be prohibitive in a large agricultural operation.

In view of the above described shortcomings of metaldehyde research has been directed toward finding new molluscicide compositions. For example, U.S. Pat. No. 3,090,723 Pastac involves a method of combatting molluscs in which metaldehyde is combined with a halogenated aldehyde derivative. Preferred halogenated aldehyde derivatives include chloral ammonia, chloral hydroxylamine, trichloracetaldoxime, arabochloralose, glucochloralose, mannochloralose, galactochloralose, chloralurethane, chloralformamide, monochloralcarbamide, and dichloralcarbamide. The Pastac composition preferably uses 0.3-3% metaldehyde and 1-3% halogenated aldehyde derivative.

U.S. Pat. No. 3,284,296 to Freiberg involves a molluscicide in the form of trialkyl tin compound having the following basic formula:

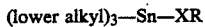

In this formula, the lower alkyl group contains from 1-6 carbon atoms. X is selected from the group consisting of oxygen and sulfur, and R is selected from the group consisting of phenyl, naphthyl, and quinolyl groups and these groups substituted with, for example, methyl, ethyl, n-pentyl, 2-methylbutyl, n-hexyl, 2-methylpentyl, and 2,2-dimethylpropyl.

Notwithstanding the above compositions, a need exists for an effective environmentally safe and economical molluscicide. The present invention represents a new and improved molluscicide composition satisfying this need, as described herein below.

SUMMARY OF THE INVENTION

It is an object of the present invention to provide a molluscicide composition which efficiently kills terrestrial molluscs, including slugs and snails.

It is another object of the present invention to provide a molluscicide composition which is environmentally safe for humans and animals.

It is another object of the present invention to provide a molluscicide composition which is economical to use and easy to apply.

Still another object of the present invention is to provide a molluscicide composition capable of killing slugs and snails under dry or moist conditions with or without the sun.

Still, another object of the present invention is to provide a molluscicide composition having an attractant therein.

A further object of the present invention is to provide a molluscicide composition which is manufactured from inexpensive commonly available materials.

A still further object of the present invention is to provide a molluscicide composition which is safe to handle and apply.

To accomplish these objectives, a molluscicide composition is provided which is highly effective and environmentally safe. The composition includes a carrier compound, an attractant and a molluscicide agent. The attractant consists of metaldehyde and the molluscicide agent consists of atomized powdered elemental aluminum. Wheat, barley, oats, corn and mill run bran are used as the carrier compound. In a preferred form of the invention, a preservative, a dispersing agent and water are added to the composition. Such materials facilitate preparation of the composition and enhance its stability. The composition may be used in meal, pellet, cake or slurry form. Regardless of the form, the composition is highly effective in killing terrestrial molluscs while avoiding the environmental and efficacy problems of other molluscicide compositions, including those using metaldehyde as the sole molluscicide agent.

These and other objects, advantages and features of the invention will become apparent hereinafter from the following detailed description and claims.

DETAILED DESCRIPTION OF A PREFERRED EMBODIMENT

The present invention represents an improved molluscicide composition having desirable efficacy and safety characteristics. The invention includes, as its primary constituents, an attractant, a molluscicide agent, a carrier and a preservative. The attractant consists of metaldehyde added in an amount between 0.005% and 3.0% by weight of the composition. Metaldehyde is commercially available from Lonza, Inc. of Fairlawn, N.J. at an approximate cost of $3.50 a lb. in small lots and $2.75 in large lots by weight.

The molluscicide agent in the composition consists of finely divided and screened atomized powdered elemental aluminum. Particle size of the atomized powdered elemental aluminum should not exceed 27 microns in diameter. Particles larger than 27 microns are undesirable, as they are too large for ingestion by many of the infant slugs and snails. The atomized powdered elemental aluminum is added in an amount between 0.005% to 3.0% by weight of the composition. Atomized powdered elemental aluminum as described here is available from the following: Alcan Powders and Chemicals, Division of Alcan Aluminum Corp. Elizabeth, N.J., Aluminum Co. of America, Atomized Metal Powders Inc., Ethyl Corporation, Reynolds Metals Co., Silberline Manufacturing Co., Inc., Transmet Corporation, U.S. Bronze Powders, Inc., Valimet, Inc., at an approximate cost of $2.00 to $2.55 per lb.

Although up to 3.0% by weight metaldehyde may be used in the invention, it is desirable that the amount used be minimized for the reasons described above. In most cases, it is not necessary for more than 0.13% by weight metaldehyde to be used. At this level, the metaldehyde functions primarily as an attractant and would not kill terrestrial molluscs if used alone. As the amount of metaldehyde is reduced, the amount of aluminum is increased within the range set forth above. The use of 0.13% aluminum in combination with 0.13% metaldehyde provides an effective slug and snail killer, as described in the Example herein below.

The increased use of aluminum in place of metaldehyde offers numerous benefits. Even if higher amounts of metaldehyde are used, e.g., 2-3%, the addition of aluminum increases the killing efficiency of the product. As noted above, atomized powdered elemental aluminum can function as a molluscicide agent in areas where the effectiveness of metaldehyde is limited. These areas primarily involve moist climates. Thus the addition of aluminum to the compositions containing metaldehyde generally increases the over-all spectrum of activity and efficacy thereof.

In addition, atomized powder elemental aluminum offers other important benefits. Because, the amount of metaldehyde required in the invention can be minimized, the environmental problems associated therewith are reduced. Atomized powdered elemental aluminum, in the concentration levels specified above, is environmentally safe for both humans and animals. The increased use of atomized powdered elemental aluminum also results in lower material costs per acre. As noted above, atomized powdered elemental aluminum is considerably less expensive than metaldehyde.

The metaldehyde and atomized powdered elemental aluminum are combined with a suitable carrier. A preferred carrier is wheat, barley, corn, oats and mill-run bran mixture materials. Approximately 99.14% by weight of carrier is preferred in the invention.

Other materials used in the invention include a dispersing agent, a preservative, and water. The water and dispersing agent facilitate even blending and production of the composition. A preferred dispersing agent is standard consumer grade beer, preferably present in an amount of 0.10% by dry weight of the composition. The beer is first added in liquid form wet at 10 pounds per 100 pounds and then dried with the rest of the mixture described below. The addition of beer during production facilitates uniform blending of the dry components in the composition. The beer also assists in minimizing dust formation during preparation of the composition. After the beer and other ingredients are dried, sugars in the beer ensure adhesion of the aluminum and metaldehyde particles to the bran, wheat, oats, barley, corn and carrier like that of a surfactant sticking agent.

Sodium propionate is a preferred preservative agent used in the invention. It is added in an amount approximately 0.50% per one hundred pounds by weight of the composition. The sodium propionate prevents microbial spoilage and extends the storage life of the product.

In addition, an auxiliary attractant may be added to the composition in variable quantities, if desired. The auxiliary attractant preferably consists of vegetable matter, decaying animal products, yeast and materials having substantial quantities of oil and/or sugars.

The final product may be applied in meal, pellet, cake or slurry form. It is usable under a variety of environmental conditions, including those involving high moisture levels. The composition will function effectively in field concentration of 100 lbs. per acre. Higher concentrations may be used if slug or snail infestation is extensive.

After application of the composition, the slugs or snails are attracted to the vinegar-like odor of the metaldehyde and the odors of any other attractant materials such as beer, wheat, oats, barley, corn and the like used in the composition. They will then ingest the atomized powdered elemental aluminum. As a result, the ingested aluminum initially causes nervous system damage and disorientation. Next, the aluminum reacts with gastrointestinal acids in the digestive systems of the slugs or snail, causing excessive hydrogen gas production and lethal physical damage to their internal tissue structure.

EXAMPLE

Tests involving the present invention have resulted in a specific formula exhibiting optimum effectiveness in destroying slugs and snails. This formula is as follows:

| Component | Percent by weight |
| --- | --- |
| Atomized powdered elemental aluminum (molluscicide agent) | 0.13% |
| Metaldehyde (attractant) | 0.13% |
| Beer (dispersing agent) | 0.10% |
| Bran, wheat, oats, barley, corn and food products (carrier) | 99.14% |
| Sodium propionate (preservative) | .50% |
| | 100.00% |

To produce a 100 pound quantity of the above composition, 0.13 lbs. of atomized powdered elemental aluminum having a particle size of between 4.5 to 6.5 microns in diameter is combined with 0.13 lbs. of metaldehyde and 0.10 lbs. of liquid beer to form a slurry. After the addition of beer, 0.50 lbs. of sodium propionate is mixed into the slurry. Thereafter, 99.14 lbs. of bran are added and the resulting combination is heated to a temperature of between 120°–180° F. and mixed at this temperature for 17–30 minutes until dry.

Tests conducted on the above composition have demonstrated a 90–100% efficiency rate in killing slugs. Similar tests involving the above composition without aluminum were also conducted. In the absence of aluminum, the composition was ineffective as a molluscicide.

Various changes and/or modifications maybe made without departing from the spirit and scope of the invention described herein as will be apparent to those skilled in the art to which it pertains. It is accordingly intended that the present invention shall only be limited by the following claim.

I claim:

1. A molluscicidal composition prepared by combining 0.13 lbs. of atomized powdered elemental aluminum, having a particle size of between 4.5 and 6.5 microns in diameter, with 0.13 lbs. of metaldehyde and 0.10 lbs. of beer to form a slurry, adding 0.50 lbs. of sodium propionate and 99.14 lbs. of bran, heating to a temperature of between 120° and 180° F. and mixing at this temperature for 17 to 30 minutes until dry.

* * * * *